United States Patent

Sofianos et al.

[11] Patent Number: 6,054,497
[45] Date of Patent: Apr. 25, 2000

[54] PROCESS FOR PRODUCING METHANOL AND CATALYST THEREFOR

[75] Inventors: Alkis Sofianos, Pretoria, South Africa; Erich Armbruster, Naters, Switzerland; Olaf Frei, Siblingen, Switzerland; Josef Heveling, Naters, Switzerland

[73] Assignee: Lonza, A.G., Gampel/Valais, Switzerland

[21] Appl. No.: 08/983,137

[22] PCT Filed: Mar. 19, 1996

[86] PCT No.: PCT/EP96/01180

§ 371 Date: Jun. 10, 1998

§ 102(e) Date: Jun. 10, 1998

[87] PCT Pub. No.: WO97/03937

PCT Pub. Date: Feb. 6, 1997

[30] Foreign Application Priority Data

Jul. 21, 1995 [CH] Switzerland .............................. 2146/95

[51] Int. Cl.[7] ............................. C07C 27/00; B01J 23/00; B01J 23/02; B01J 23/70

[52] U.S. Cl. .......................... 518/713; 518/700; 502/307; 502/344; 502/345; 502/349

[58] Field of Search ..................................... 518/713, 700; 502/307, 344, 345, 349

[56] References Cited

U.S. PATENT DOCUMENTS

| 4,149,009 | 4/1979 | Yoneoka et al. |
|---|---|---|
| 4,780,481 | 10/1988 | Courty et al. ........................... 518/713 |
| 5,254,520 | 10/1993 | Sofianos. |

FOREIGN PATENT DOCUMENTS

| 0 255 295 | 7/1987 | European Pat. Off. . |
|---|---|---|
| 2 151 498A | 7/1985 | United Kingdom . |

OTHER PUBLICATIONS

Y. Nitta et al. Catal. Lett., 26, (1994) 345–354.

*Primary Examiner*—Gary Geist
*Assistant Examiner*—J. Parsa
*Attorney, Agent, or Firm*—Fisher, Christen & Sabol

[57] ABSTRACT

A process for the synthesis of methanol on X-ray amorphous catalysts with a copper, zinc and zirconium oxide content in relative proportions of 10 to 70 weight percent of copper, 10 to 50 weight percent of zinc and 20 to 80 weight percent of zirconium. The process for the synthesis of methanol is distinguished by high space time yields.

14 Claims, 2 Drawing Sheets

6,054,497

PROCESS FOR PRODUCING METHANOL AND CATALYST THEREFOR

This application is a 371 of PCT/EP 96/01180 filed Mar. 19, 1996.

BACKGROUND OF THE INVENTION

1. Field of the Invention

The present invention relates to a process for preparing methanol by reacting a gas mixture containing hydrogen and carbon monoxide and/or carbon dioxide over a catalyst.

2. Background Art

It is known that methanol can be prepared from H and CO and/or $CO_2$ over copper-containing catalysts. It is also known that catalysts containing not only copper but also zinc oxide, zirconium oxide and, if desired, further oxides can be used for this purpose (GB-A 2 151 498, U.S. Pat. No. 5,254,520, Y. Nitta et al., *Catal. Lett.* 1994, 26, 345–354). Although the catalysts known hitherto do give usable space-time yields in the synthesis of methanol, it is desirable to increase these further. Moreover, the known catalysts frequently contain additives which make it more difficult to dispose of or reprocess the used catalyst. It is therefore an object of the invention to provide, by use of an improved catalyst, a methanol-preparation process having a higher space-time yield, where the catalyst should if possible contain no toxic or otherwise harmful components.

BROAD DESCRIPTION OF THE INVENTION

According to the invention, this object is achieved by the process of the invention. It has surprisingly been found that good results can be achieved even with a catalyst having the simple composition of 10–70% of Cu, 10–50% of Zn and 20–80% of Zr if it is essentially X-ray-amorphous. The percentages indicate the relative proportions of the metallic elements Cu, Zn and Zr, i.e. the sum of the three values is always 100% regardless of whether further elements are present. Indicating the composition in per cent by weight of the metals (and not the metal oxides) is advantageous here because changes in the oxidation state during the course of preparation, activation or use of the catalyst can have no influence on these figures. Here and in the following, the catalyst in the context of all indications of the composition is only the catalytically active substance. This can, of course, be applied to a support or be converted into a ready-to-use form in another way. For the purposes of the present invention, the term "essentially X-ray-amorphous" refers to a catalyst whose X-ray diffraction pattern has, like that of a liquid or a glass, no discrete diffraction lines.

The catalyst used according to the invention preferably contains 20–50% of Cu, 10–40% of Zn and 30–60% of Zr.

The catalyst is preferably prepared by precipitating a precursor from a solution of water-soluble copper, zinc and zirconium salts by coprecipitation. This is washed and dried and subsequently calcined at 300–500° C. In this temperature range, no appreciable crystallization of the amorphous catalyst precursor takes place. Before use in the synthesis of methanol, the catalyst is advantageously activated. This is achieved by heating in a hydrogen-containing atmosphere to a final temperature of from 200 to 350° C. Preferably, the catalyst is first held at a low temperature in an inert atmosphere, for example under nitrogen or argon, and then subjected stepwise or continuously to slowly increasing temperatures and hydrogen concentrations until the final temperature is reached.

As water-soluble copper, zinc and zirconium salts, preference is given to using the chlorides or nitrates.

The coprecipitation is preferably effected by adding an alkali metal hydroxide solution to the solution of the water-soluble copper, zinc and zirconium salts. The coprecipitation can be carried out continuously or batchwise and, in any case, intensive mixing of the reactants has to be ensured.

The methanol synthesis itself can be carried out under the customary temperature and pressure conditions. The temperature is advantageously from 200 to 320° C., preferably from 220 to 280° C. The pressure is advantageously in the range from 1 to 10 MPa, preferably from 3 to 7 MPa.

The methanol synthesis using the catalysts of the invention is preferably carried out at a gas hourly space velocity (GHSV) of from 3200 to 40,000 ml/(g·h) (based on STP), particularly preferably at from 5000 to 20,000 ml/(g·h).

DETAILED DESCRIPTION OF THE INVENTION

The following examples illustrate how the process of the invention is carried out:

Example 1

Preparation of the Catalyst from the Chlorides

To prepare a catalyst containing 25% of Cu, 25% of Zn and 50% of Zr, 625.3 g of zinc chloride and 804.8 g of copper(II) chloride dihydrate were each dissolved in 1.4 l of deionized water. The two solutions were subsequently combined and admixed with 4.242 kg of a zirconyl chloride solution containing 1.172 kg of $ZrOCl_2$. The solutions were mixed well and diluted further with 1.8 l of water. Precipitation was subsequently carried out over a period of 1–2 hours at a pH of 8.5 using 30% strength sodium hydroxide solution while stirring intensively (Ultra-Turrax®). The remainder of the stoichiometrically required amount of sodium hydroxide was then added. The precipitate was filtered off at 1.8 bar in a chamber filterpress and washed with deionized water until the pH of the washings was less than 8.0 and the chloride content of the filtercake was less than 0.01%. The filtercake was dried at 100° C., treated once more with water and dried again at 100° C. The X-ray diffraction pattern of a sample of the dried material was recorded (FIG. 1, curve 1) and this showed that the material was completely amorphous. The dried catalyst precursor was subsequently heated in 50 K steps from 100° C. to 300° C. and held at each temperature stage for 30 minutes. The temperature was finally increased to 350° C. and held at this value for 3 hours. After this calcination, the catalyst had the following properties:

BET surface area: 75 $m^2/g$
Cu surface area: 10.9 $m^2/g$ (determined by $N_2O$ chemisorption)

Figure 2:
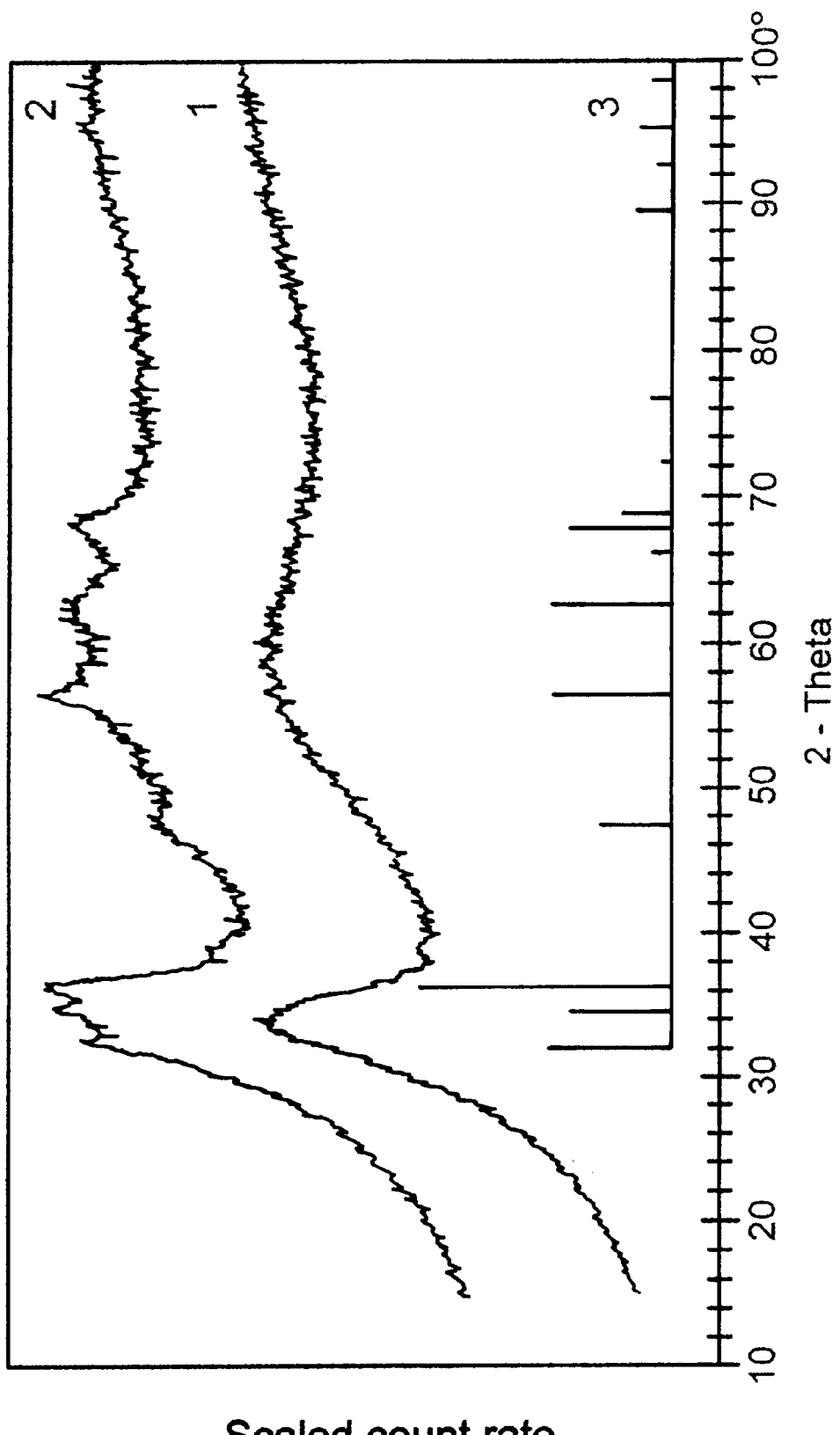
FIG. 2 shows the X-ray diffraction patterns of the catalysts from Example 1 (1) and the comparative example (2) after calcination and also the diffraction lines of synthetic zincite (ZnO) [JCPDS 361451] (3).

Crystallite size: <2 nm (X-ray-amorphous), for X-ray diffraction patterns see FIG. 2 (1).

Example 2

A catalyst having the composition 40% of Cu, 20% of Zn and 40% of Zr was prepared by a method similar to Example 1, but using the corresponding nitrates as starting materials in place of the chlorides. Before calcination, the catalyst obtained in this way had a BET surface area of 177 m$^2$/g and was completely X-ray-amorphous. The calcined sample was likewise completely X-ray-amorphous and had a BET surface area of 62 m$^2$/g.

Comparative Example

Figure 1:
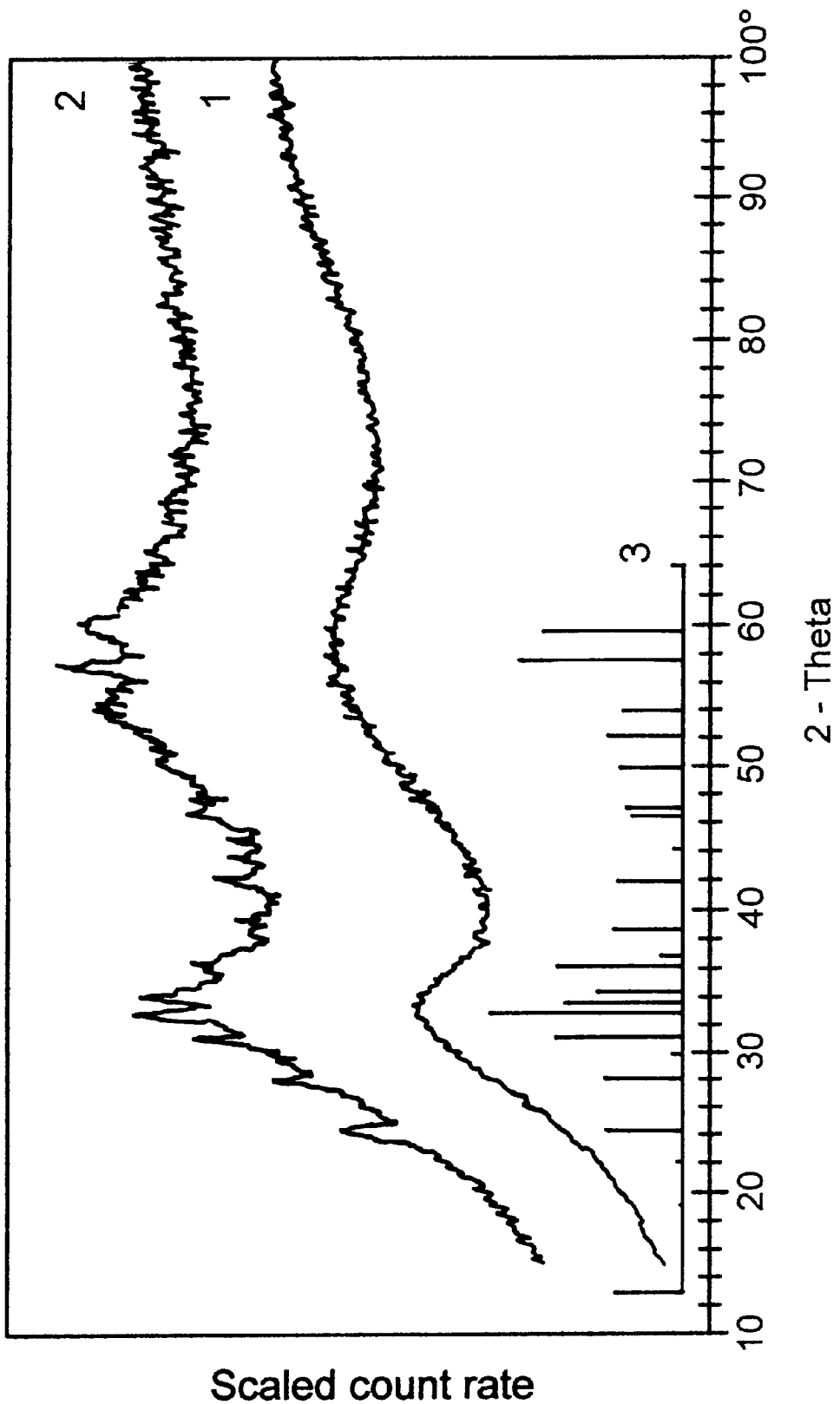
FIG. 1 shows the X-ray diffraction patterns of the catalyst precursors, i.e. in each case before calcination, from Example 1 (curve 1) and the comparative example (2), and also the diffraction lines of the crystalline reference substance $(Cu_{0.2}Zn_{0.8})_5(CO_3)_2(OH)_6$ from the databank of the "Joint Committee on Powder Diffraction Standards" (International Center for Diffraction Data, 1601 Park Lane, Swarthmore Pa. 19081, USA) [JCPDS 380154] (3).

Using the method of GB-A 2 151 498, Example 1, a Cu/Zn/Zr catalyst having the composition 29% of Cu. 23% of Zn and 48% of Zr, but without addition of chromium, was prepared:

A solution of 317.4 g of copper(II) nitrate trihydrate, 294.5 g of zinc nitrate hexahydrate and 400.9 g of zirconyl nitrate dihydrate in 10 l of water was heated to 60° C. and added at 60° C. while stirring vigorously to a solution of 631 g of ammonium hydrogen carbonate in 30 l of water. The mixture was stirred further for 1 hour at 60° C. The temperature was then held at 80° C. for 30 minutes and the mixture was finally stirred at this temperature for a further 30 minutes. After cooling, the precipitate was filtered off, washed four times with 10 l each time of water and subsequently kneaded for 2 hours in a kneader. A suspension having a solids content of 16% was then prepared by addition of 1.25 l of water and this suspension was dried in a spray drier (air inlet temperature: 220° C.). The X-ray diffraction pattern of the dried material was recorded.. This pattern displayed, superimposed on a continuous background, a distinct structure which could be assigned to the diffraction lines of $(Cu,Zn)_5(CO_3)_2(OH)_6$ (FIG. 1, curve 2). The material was accordingly partially crystalline. Finally, the material was calcined for 2 hours at 380° C. The X-ray diffraction pattern of the catalyst obtained in this way was also recorded (FIG. 2, curve 2). This displayed, superimposed on an unstructured background, reflections which could be assigned to the mineral zincite (ZnO). The calcined material was thus also partially crystalline.

Example 3

The catalysts described in Examples 1 and 2 and the comparative example were tested for their suitability for the synthesis of methanol. The reaction was carried out in fixed-bed microreactors (18 mm Ø). The $CO+CO_2$ conversion, the yield of methanol, the methanol selectivity and the space-time yield were determined. The analysis of the reaction products was carried out by on-line gas chromatography. The catalyst activity is indicated by the conversion of $CO+CO_2$, the methanol yield, the selectivity (in each case in mol% based on the carbon in the synthesis gas) and the space-time yield in kg/(kg·h) (=kg per kg of catalyst and hour).

The catalysts were activated in situ as follows: under nitrogen (0.8 MPa), the reactor was slowly heated to 130° C. 2% of hydrogen were then mixed into the nitrogen and the temperature was increased at 20 K/h to 200° C. After 16 hours, the proportion of hydrogen was increased to 12%, the temperature was raised to 240° C. and was held at this level for 2 hours.

The methanol synthesis was carried out at 250° C. and 5 MPa. The starting material used was a synthesis gas mixture containing 32% by volume of carbon monoxide, 5% by volume of carbon dioxide and 63% by volume of hydrogen. The space velocity was 8000 ml/(g·h). The results (conversion, yield, selectivity and space-time yield) are shown in Table 1 below. The values given are in each case those measured after a reaction time of 49 hours, i.e. after a steady state has been reached.

TABLE 1

| Catalyst from: | Conversion [mol%] | Yield [mol%] | Selectivity [mol%] | Space-time yield [kg/(kg · h)] |
|---|---|---|---|---|
| Example 1 | 10.05 | 9.57 | 95.3 | 0.41 |
| Example 2 | 13.58 | 12.70 | 93.5 | 0.54 |
| Comparative Example 1 | 10.00 | 8.71 | 87.1 | 0.37 |

Examples 4–6

Using a method similar to Example 2, further catalysts having various compositions were prepared. The stirrer used in the continuous coprecipitation in these examples was the model Polytron® PT45-80. The composition in % by weight and the precipitation conditions (temperature θ, pH, concentration c, stirring frequency v and addition rate n) are shown in Table 2 below.

TABLE 2

| Example No. | Cu:Zn:Zr [% by weight] | θ [° C.] | pH | c [mol NO$_3$/kg] | v [min$^{-1}$] | n [mol NO$_3$/min] |
|---|---|---|---|---|---|---|
| 4 | 37.5:12.5:50 | 50 | 9.5 | 1.48 | 3000 | 0.035 |
| 5 | 35:35:30 | 10 | 9.5 | 1.45 | 3000 | 0.025 |
| 6 | 40:20:40 | 30 | 10.5 | 2.01 | 3500 | 0.030 |

To characterize the catalysts, the specific surface areas were determined by the BET method and X-ray diffraction patterns (XRD) were recorded in each case both before and after calcination. The results are shown in Table 3 below.

TABLE 3

| Example No. | Cu:Zn:Zr [% by weight] | BET$^{(1)}$ [m$^2$/g] | BET$^{(2)}$ [m$^2$/g] | XRD$^{(1)}$ | XRD$^{(2)}$ |
|---|---|---|---|---|---|
| 4 | 37.5:12.5:50 | 211 | n.d. | amorphous | amorphous |
| 5 | 35:35:30 | 136 | n.d. | amorphous | amorphous |
| 6 | 40:20:40 | 163 | n.d. | amorphous | amorphous |

$^{(1)}$before calcination
$^{(2)}$after calcination

In the synthesis of methanol, the results shown in Table 4 below were achieved after a reaction time of 55 hours under the conditions specified in Example 3:

TABLE 4

| Example No. | Cu:Zn:Zr [% by weight] | Conversion [mol%] | Yield [mol%] | Selectivity [mol%] | Space-time yield [kg/(kg · h)] |
|---|---|---|---|---|---|
| 4 | 37.5:12.5:50 | 13.10 | 11.04 | 84.3 | 0.44 |
| 5 | 35:35:30 | 15.10 | 13.20 | 87.4 | 0.52 |
| 6 | 40:20:40 | 14.85 | 13.40 | 90.2 | 0.53 |

We claim:
1. A process comprising preparing methanol from a gas mixture containing hydrogen and carbon monoxide and/or carbon dioxide in the presence of a catalyst consisting essentially of copper oxide, zinc oxide and zirconium oxide, the catalyst containing the elements copper, zinc and zirconium in relative proportions of from 10 to 70 percent by weight of Cu, from 10 to 50 percent by weight of Zn and from 20 to 80 percent by weight of Zr, and being essentially X-ray-amorphous.

2. The process according to claim 1, wherein the catalyst contains the elements copper, zinc and zirconium in relative proportions of from 10 to 70 percent by weight of Cu, from 10 to 50 percent by weight of Zn and from 20 to 80 percent by weight of Zr, and being essentially X-ray-amorphous, with the proviso that said catalyst does not contain any cobalt.

3. The process according to claim 1, wherein the catalyst is prepared by coprecipitation of a precursor from a solution of water-soluble copper, zinc, and zirconium salts and optionally further additives, washing, drying, calcination of the dried precursor at from 300° to 500° C. and activation at from 200° to 350° C. in a hydrogen-containing atmosphere.

4. The process according to claim 3, wherein the solution of water-soluble copper, zinc, and zirconium salts which is used is a solution of the chlorides and/or nitrates.

5. The process according to claim 3, wherein the coprecipitation is carried out by addition of an alkali metal hydroxide solution to the solution of the water-soluble copper, zinc, and zirconium salts.

6. The process according to claim 3, wherein the catalyst is prepared by coprecipitation of a precursor from a solution of water-soluble copper, zinc and zirconium salts and optionally further additives, washing, drying, calcination of the dried precursor at 300° to 500° C. and activation at from 200° to 350° C. in a hydrogen-containing atmosphere.

7. The process according to claim 6, wherein the solution of water-soluble copper, zinc and zirconium salts which is used is a solution of the chlorides and/or nitrates.

8. The process according to claim 7, wherein the coprecipitation is carried out by addition of an alkali metal hydroxide solution to the solution of the water-soluble copper, zinc and zirconium salts.

9. A catalyst containing copper oxide, zinc oxide and zirconium oxide, for the synthesis of methanol, the elements copper, zinc and zirconium being in proportions of from 10 to 70 percent by weight of Cu, from 10 to 50 percent by weight of Zn and from 20 to 80 percent by weight of Zr, and being essentially X-ray-amorphous, with the proviso that said catalyst contains less than 5 percent by weight of a cobalt.

10. A catalyst consisting essentially of copper oxide, zinc oxide and zirconium oxide, for the synthesis of methanol, the elements copper, zinc and zirconium being in proportions of from 10 to 70 percent by weight of Cu, from 10 to 50 percent by weight of Zn and from 20 to 80 percent by weight of Zr, and being essentially X-ray-amorphous.

11. A process for preparing the catalyst according to claim 9, wherein a catalyst precursor is precipitated from a solution of water-soluble copper, zinc, and zirconium salts and optionally, further additives, by coprecipitation and this is washed, dried, calcined at from 300° to 500° C. and activated at from 200° to 350° C. in a hydrogen-containing atmosphere.

12. The process according to claim 11, wherein the solution of water-soluble copper, zinc, and zirconium salts which is used is a solution of the chlorides and/or nitrates.

13. The process according to claim 12, wherein the coprecipitation is carried out by addition of an alkali metal hydroxide solution to the solution of the water-soluble copper, zinc and zirconium salts.

14. The process according to claim 11, wherein the coprecipitation is carried out by addition of an alkali metal hydroxide solution to the solution of the water-soluble copper, zinc and zirconium salts.

* * * * *